United States Patent [19]

Preuilh et al.

[11] Patent Number: 6,106,848
[45] Date of Patent: *Aug. 22, 2000

[54] TOPICALLY APPLICABLE O/W EMULSIONS HAVING HIGH GLYCOL CONTENT AND AT LEAST ONE BIOLOGICALLY ACTIVE AGENT

[75] Inventors: Isabelle Preuilh, Le Canet; Nathalie Willcox, Le Rouret, both of France

[73] Assignee: Centre International de Recherches Dermatologiques, Valbonne, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/935,054

[22] Filed: Sep. 22, 1997

[30] Foreign Application Priority Data

Sep. 20, 1996 [FR] France .................................... 96 11510

[51] Int. Cl.$^7$ ............................ A61K 9/07; A61K 47/10; A61K 47/14; A61K 47/30
[52] U.S. Cl. .............................. 424/401; 424/59; 424/62; 424/63; 424/65; 424/70.1; 424/70.6; 424/70.8; 424/70.9; 424/70.11; 424/70.16; 424/70.21; 424/70.22; 424/73; 523/105; 523/122; 514/818; 514/852; 514/859; 514/864; 514/875; 514/880; 514/882; 514/886; 514/887; 514/937; 514/938; 514/939; 514/940; 514/941

[58] Field of Search ...................................... 523/102–105, 523/122; 524/386; 510/158–160; 574/817, 818, 825, 828, 844–848, 852, 855, 865, 871, 873–875, 880–882, 886, 887, 928, 937–941, 947; 424/405, 401, 59

[56] References Cited

FOREIGN PATENT DOCUMENTS

| | | |
|---|---|---|
| 0268164 | 5/1988 | European Pat. Off. . |
| 0279641 | 8/1988 | European Pat. Off. . |
| 0347225 | 12/1989 | European Pat. Off. . |
| 2646435 | 4/1978 | Germany . |
| 94/17830 | 8/1994 | WIPO . |

*Primary Examiner*—Neil S. Levy
*Attorney, Agent, or Firm*—Burns, Doane, Swecker & Mathis, L.L.P.

[57] ABSTRACT

Stable, topically applicable oil-in-water bioaffecting emulsions having intermediate viscosity, characteristically ranging from 3 to 10 Pa·s, comprise (a) from 30% to 50% by weight of at least one pro-penetrating glycol, (b) at least one emulsifying agent, advantageously an anionic amphiphilic polymer, and (c) at least one biologically active agent, for example an active agent that modulates skin differentiation and/or proliferation and/or pigmentation, an anti-inflammatory, an antibacterial, an antifungal, etc.

20 Claims, No Drawings

TOPICALLY APPLICABLE O/W EMULSIONS HAVING HIGH GLYCOL CONTENT AND AT LEAST ONE BIOLOGICALLY ACTIVE AGENT

This application claims benefit of priority under 35 U.S.C. §119 to French Application No. 96-11510, filed on Sep. 20, 1996.

BACKGROUND OF THE INVENTION

1. Technical Field of the Invention

The present invention relates to novel topically applicable oil-in-water (O/W) emulsions comprising a high content of at least one pro-penetrating glycol, an appropriate emulsifying system and at least one biologically active agent.

2. Description of the Prior Art

Currently marketed are numerous topical compositions comprising an active agent and a high content of glycol, the latter promoting the penetration of the biologically active agent into the skin. Given the high content of pro-penetrating glycol, these compositions are formulated as emulsions having a high content of fatty phase which are also commonly designated "lipocreams," as anhydrous compositions which are deemed "ointments," as fluid compositions having a high content of volatile solvents, such as ethanol or isopropanol, which are destined for application to the scalp, i.e., "hair lotions," or, alternatively, as viscous O/W emulsions which are also designated "O/W creams."

O/W creams comprising a corticoid and including a high percentage of propylene glycol (47.5%), which are marketed under the trademark TEMOVATE® by GLAXO, are known to this art. Indeed, the stabilization of a formulation comprising such a percentage of glycol necessitates incorporating, in the emulsion, emulsifying and stabilizing agents of the glyceryl stearate or PEG 100 stearate type or, alternatively, stabilizing agents or consistency factors of the white wax or ketostearyl alcohol type which form a viscous cream, namely, whose viscosity is greater than 10 Pa·s (10,000 centipoises, measured with a Brookfield apparatus model LVDV II+paddle No. 4, at a speed of 30 revolutions/min for 30 seconds and at a temperature of 25° C.±3° C.).

To facilitate the application of topical compositions comprising a high percentage of glycol, it would be desirable to provide novel formulations of the O/W emulsion type, whose viscosity would be intermediate between the hair lotions which are too fluid and the use of which is too limited, and the O/W creams which are too viscous and which have a fatty and sticky characteristic, while preserving the propenetrating properties of the glycol.

SUMMARY OF THE INVENTION

Accordingly, a major object of the present invention is the provision of novel topically applicable oil-in-water (O/W) emulsions, comprising from 30% to 50% by weight relative to the total weight of the composition of at least one glycol, an appropriate emulsifying system and at least one biologically active agent.

DETAILED DESCRIPTION OF BEST MODE AND SPECIFIC/PREFERRED EMBODIMENTS OF THE INVENTION

More particularly according to the present invention, by "fluid emulsion" is advantageously intended an emulsion whose viscosity ranges from 3 to 10 Pa·s (3,000 to 10,000 centipoises), a viscosity measured with a Brookfield apparatus model LVDV II+paddle No. 4, at a speed of 30 revolutions/min for 30 seconds and at a temperature of 25° C.±3° C.

Advantageously, a stable emulsion is provided according to the invention by selecting, as an appropriate emulsifying system, at least one polymeric emulsifier. The polymeric emulsifiers are in particular described by CLYMANS & BRAND in "Cosmetics and Toiletries" (manufacture worldwide, 1995, 119–125).

These are, in particular, anionic amphiphilic polymers, more especially those comprising at least one hydrophilic recurring structural unit of the unsaturated olefin carboxylic acid type, and at least one hydrophobic recurring structural unit of the $C_{10}$–$C_{30}$ alkyl ester type.

According to the invention, acrylic structural units are those of the formula:

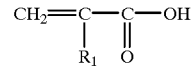

in which $R_1$ is H, $CH_3$ or $C_2H_5$, namely, acrylic acid, methacrylic acid or ethacrylic acid structural units.

Alkyl acrylate structural units are those of the formula:

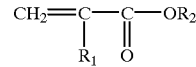

in which $R_1$ is H, $CH_3$ or $C_2H_5$, namely, acrylate, methacrylate or ethacrylate units, and $R_2$ is a $C_{10}$–$C_{30}$, preferably $C_{12}$–$C_{22}$, alkyl radical.

Exemplary acrylates according to the invention include lauryl acrylate, stearyl acrylate, decyl acrylate, isodecyl acrylate, dodecyl acrylate and the corresponding methacrylates, lauryl methacrylate, stearyl methacrylate, decyl methacrylate, isodecyl methacrylate and dodecyl methacrylate.

Preferably, the above anionic amphiphilic polymers are crosslinked using a crosslinking polymerizable comonomer containing a $CH_2$=C< group with at least one other polymerizable group whose sites of unsaturation are not conjugated relative to each other.

Exemplary such crosslinking polymerizable comonomers preferably include polyallyl ethers such as, in particular, polyallylsucrose and polyallylpentaerythritol.

Crosslinked polymers of this type are well known to this art; they are, in particular, described in U.S. Pat. Nos. 3,915,921 and 4,509,949.

According to the invention, anionic amphiphilic polymers are preferred which comprise 95% to 60% by weight of acrylic recurring structural units, 4% to 40% by weight of acrylate recurring structural units and 0.1% to 6% by weight of crosslinking monomer, or (ii) which comprise 98% to 96% by weight of acrylic recurring structural units, 1% to 4% by weight of acrylate recurring structural units and 0.1% to 0.6% by weight of crosslinking monomer.

Among said crosslinked polymers indicated above, those marketed by GOODRICH under the trademarks PEMULEN TR1, PEMULEN TR2, CARBOPOL 1342 and CARBOPOL 1382 are most particularly preferred according to the present invention.

The compositions according to the invention advantageously comprise up to 1 by weight of appropriate emulsifying system, preferably from 0.2% to 0.4% by weight relative to the total weight of the composition.

The pro-penetrating glycol is advantageously selected from among propylene glycol, dipropylene glycol, propylene glycol dipelargonate, lauroglycol or ethoxydiglycol.

Preferably, the compositions according to the invention comprise from 40% to 50% by weight of pro-penetrating glycol.

Exemplary active agents according to this invention include the agents modulating skin differentiation and/or proliferation and/or pigmentation such as retinoic acid and isomers thereof, retinol and esters thereof, retinal, retinoids, in particular those described in FR-2,570,377, EP-199,636, EP-325,540, EP-402,072, vitamin D and derivatives thereof, estrogens such as estradiol, kojic acid or hydroquinone; antibacterial agents such as clindamycin phosphate, erythromycin or the tetracycline class of antibiotics; antiparasitic agents, in particular metronidazol, crotamiton or pyrethrinoids; antifungal agents, in particular compounds belonging to the class of imidazoles such as econazole, ketoconazole or miconazole or salts thereof, polyene compounds such as amphotericin B, compounds of the family of allylamines, such as terbinafine or alternatively octopirox; steroidal anti-inflammatory agents such as hydrocortisone, anthralins (dioxyanthranol), anthranoids, betamethasone valerate or clobetasol propionate, or non-steroidal anti-inflammatory agents such as ibuprofen and salts thereof, diclofenac and salts thereof, acetylsalicylic acid, acetaminophen or glycyrrhetinic acid; anaesthetic agents such as lidocaine hydrochloride and derivatives thereof; antipruritic agents such as thenaldine, trimeprazine or cyproheptadine; antiviral agents such as acyclovir; keratolytic agents such as alpha- and beta-hydroxycarboxylic or beta-ketocarboxylic acids, their salts, amides or esters and more particularly the hydroxy acids such as glycolic acid, lactic acid, malic acid, salicylic acid, citric acid and, in general, the fruit acids, and 5-n-octanoylsalicylic acid; anti-free radical agents such as alpha-tocopherol or esters thereof, superoxide dismutases, certain metal chelators or ascorbic acid and esters thereof; antiseborrhoeic agents such as progesterone; antidandruff agents such as octopirox or zinc pyrithione; anti-acne agents such as retinoic acid, benzoyl peroxide or adapalene; antimetabolites; agents for combating hair loss such as minoxidil; antiseptics.

Advantageously, the compositions according to the invention comprise from 0.0001% to 20% by weight relative to the total weight of the composition of at least one active agent, preferably from 0.025% to 15% by weight.

Of course, the amount of active agent in the compositions according to the invention will depend on the active agent under consideration. Thus, for a steroidal anti-inflammatory agent, the compositions according to the invention will advantageously comprise less than 1% by weight of active agent, preferably from 0.025% to 0.05% by weight. For the hydroquinones, the compositions according to the invention will preferably comprise from 2% to 5% of active agent. For the antibacterial or antifungal agents such as econazole, the compositions of this invention will preferably comprise from 8% to 10% by weight of active agent.

The fatty phase of the emulsion according to the invention may comprise fatty substances normally used in the intended field of application.

Among these, representative are the silicone fatty substances such as the silicone oils, as well as the non-silicone fatty substances such as the vegetable, mineral, animal or synthetic oils.

Exemplary silicone fatty substances include:
(i) the poly($C_1$–$C_{20}$ alkyl)siloxanes and, in particular, those having trimethylsilyl terminal groups, preferably those whose viscosity is less than 0.06 m²/s, among which are included the linear polydimethylsiloxanes and the alkylmethylpolysiloxanes such as cetyldimethicone (CTFA name),
(ii) the volatile silicone oils, such as:
   (a) the cyclic volatile silicones having from 3 to 8 silicon atoms and preferably from 4 to 5; these include, for example, cyclotetradimethylsiloxane, cyclopentadimethylsiloxane or cyclohexadimethylsiloxane,
   (b) the cyclocopolymers of the dimethylsiloxane/methylalkylsiloxane type, such as SILICONE FZ 3109 marketed by UNION CARBIDE, which is a dimethylsiloxane/methyloctylsiloxane cyclocopolymer,
   (c) the linear volatile silicones having from 2 to 9 silicon atoms; these include, for example, hexamethyldisiloxane, hexyl heptamethyltrisiloxane or octyl heptamethyltrisiloxane,
(iii) the phenylated silicone oils, in particular those having the structural formula (I):

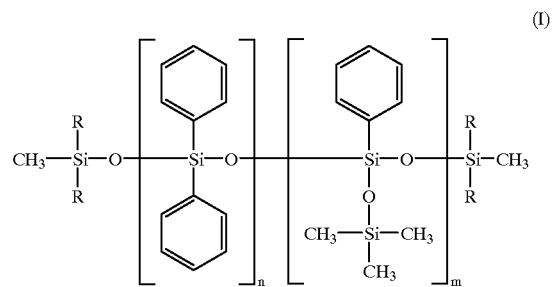

in which R is a $C_1$–$C_{30}$ alkyl radical, an aryl radical or an aralkyl radical; n is an integer ranging from 0 to 100, and m is an integer ranging from 0 to 100, with the proviso that the sum n+m ranges from 1 to 100.

Among the nonsilicone fatty substances, exemplary are the conventional oils such as paraffin oil, petroleum jelly, almond oil, perhydrosqualene, apricot oil, wheat germ, sweet almond, calophyllum, palm, castor, avocado, jojoba, olive or cereal germ oil; esters of fatty acids or of fatty alcohols, such as octyl dodecyl myristate or $C_{12}$–$C_{15}$ alkyl benzoates, alcohols; acetylglycerides; octanoates, decanoates or ricinoleates of alcohols or of polyalcohols; triglycerides of fatty acids; glycerides; hydrogenated polyisobutene, hydrogenated oils which are solid at 25° C.; lanolins; fatty esters which are solid at 25° C.

These fatty substances may, in particular, be variously selected by one skilled in this art such as to provide a composition having the desired properties, for example as regards consistency or texture.

Thus, the fatty phase of the emulsion according to the invention may constitute from 5% to 50% by weight relative to the total weight of the composition, and preferably from 15% to 25% by weight.

The aqueous phase of the emulsions according to the invention may comprise water, a floral water such as cornflower water, or a natural mineral or thermal water, for example selected from among Vittel water, water from the Vichy basin, Uriage water, Roche Posay water, Bourboule water, Enghien-les-Bains water, Saint Gervais-les-Bains water, Nèris-les-Bains water, Allevard-les-Bains water, Digne water, Maizières water, Neyrac-les-Bains water, Lons-le-Saunier water, Bonnes water, Rochefort water, Saint Christau water, Fumades water, Tercis-les-bains water, Avène water or Aix les Bains water.

The aqueous phase advantageously comprises from 10% to 70% by weight relative to the total weight of the composition, preferably from 20% to 40% by weight.

The pH of the compositions according to the invention advantageously ranges from 5 to 7, preferably from 5.5 to 6.5. It will be adjusted to the desired value by adding customary inorganic or organic bases or acids.

Moreover, the compositions according to the invention may comprise from 0% to 3% by weight, preferably from 0% to 2% by weight, relative to the total weight of the composition, of at least one coemulsifier which is advantageously selected from among esters of saturated or unsaturated fatty acids, which are natural or synthetic, in particular oleic acid or (iso)stearic acid, such as the esters of polyglycerin and isostearic acid which are marketed under the trademark LAMEFORM TGI by SIDOBRE-SINNOVA HENKEL, sorbitan isostearate marketed under the trade mark ARLACEL 987 by ICI, sorbitan sesquioleate marketed under the trademark ARLACEL 83 by ICI, the esters of glycol and isostearic acid such as PEG-6 isostearate marketed under the trademark OLEPAL ISOSTEARIQUE by GATTEFOSSE, the esters of sorbitol and oleic acid such as the polysorbates marketed under the trademark TWEEN by ICI, the fatty alcohol ethers, in particular oleyl alcohol, in particular the esters of glycol and oleyl alcohol, such as the oleths marketed under the trademark BRIJ by ICI, oxyethylenated sorbitan monostearate, the fatty alcohols such as stearyl alcohol or cetyl alcohol.

In addition, the compositions according to the invention may comprise at least one gelling and/or thickening agent in preferred concentrations ranging from 0% to 5% by weight relative to the total weight of the composition.

The gelling and/or thickening agent is advantageously selected from among:
(a) the polysaccharide biopolymers such as xanthan gum, carob gum, guar gum, alginates, modified celluloses such as hydroxyethylcellulose, methylcellulose, hydroxypropylcellulose, hydroxypropylmethylcellulose and carboxymethylcellulose,
(b) the synthetic polymers such as the polyacrylic acids, for example, glyceryl poly(meth)acrylate polymers such as HISPAGEL or LUBRAGEL marketed by HISPANO QUIMICA or GARDIAN, polyvinylpyrrolidone, polyvinyl alcohol, the crosslinked polymers of acrylamide and ammonium acrylate such as PAS 5161 or BOZEPOL C marketed by HOECHST, the crosslinked polymers of acrylamide and partially or completely neutralized 2-acrylamido-2-methylpropanesulfonic acid such as SEPIGEL 305 marleted by SEPPIC, the crosslinked polymers of acrylamide and methacryloyloxyethyltrimethylammonium chloride such as SALCARE SC 92 marketed by ALLIED COLLOIDS, the crosslinked polymers of acrylic acid and alkyl ethers of sucrose or of pentaerythritol (carbomers) such as CARBOPOL 910 to 934 marketed by GOODRICH.

The subject emulsions may comprise, in addition, any additive or adjuvant customarily employed in the cosmetic or pharmaceutical field, such as antioxidants, colorants, perfumes, essential oils, preservatives, cosmetic active agents, moisturizers, vitamins, essential fatty acids, sphingolipids, selftanning compounds such as DHA, sunscreening agents, fat-soluble polymers, in particular those which contain hydrocarbons, such as polybutene, polyalkylenes, polyacrylates and silicone polymers which are compatible with fatty substances. Of course, one skilled in this art will take care to select this or these possible additional compound(s), and/or their quantity, such that the advantageous properties of the compositions according to the invention are not, or not substantially, altered by the intended addition.

These additives and adjuvants may be present in the subject compositions in an amount of 0% to 10% by weight relative to the total weight of the composition.

In order to further illustrate the present invention and the advantages thereof, the following specific examples are given, it being understood that same are intended only as illustrative and in nowise limitative.

In said examples to follow, all parts and percentages are given by weight.

EXAMPLE 1

Example of a Specific Formulation According to the Invention

| COMPOSITION: | % by weight |
| --- | --- |
| Purified water | qs 100 |
| Hydroxypropylmethylcellulose | 0.10 |
| Propylene glycol | 47.50 |
| Active agent | 0.05 |
| Liquid paraffin 110–230 | 20.00 |
| Acrylate/$C_{10}$–$C_{30}$ alkyl acrylate crosslinked polymer (marketed under the trademark PEMULEN TR-2 by GOODRICH) | 0.30 |
| PEG-6 isostearate | 2.00 |
| NaOH, 10% | qs pH 6 |

In this formulation, the active agent remained stable for at least 3 months at 40° C.

EXAMPLE 2

Activity of Formulation Comprising Clobetasol Propionate

The formulation of Example 1 according to the invention comprised clobetasol propionate as the active agent.

Vasoconstriction tests according to the modified Stoughton protocol were performed in comparison with the corresponding O/W cream marketed under the trademark TEMOVATE by GLAXO.

The results evidenced an identical bioactivity for the two formulae, which confirmed that, despite the modification of the viscosity of the formulation according to the invention and the use of a different emulsifying system, the propenetrating glycol retained its pro-penetrating properties.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable, topically applicable oil-in-water emulsion which is topically applicable to skin having intermediate viscosity, comprising (a) from 30% to 50% by weight relative to the total weight of said emulsion of at least one glycol, (b) at least one emulsifying agent comprising an anionic amphiphilic polymer, and (c) at least one biologically active agent, wherein said anionic amphiphilic polymer is present in an amount which in the absence of another emulsifying agent results in an emulsion having an intermediate viscosity, wherein said intermediate viscosity is a viscosity which ranges from 3 to 10 Pa·s (3,000 to 10,000 centipoises), measured with a Brookfield viscometer LVDV II+paddle No. 4, at a speed of 30 revolutions/minutes for thirty seconds, and at a temperature of 25° C.±3° C.

2. The oil-in-water emulsion as defined by claim 1, comprising up to 5% by weight relative to the total weight of said emulsion of at least one gelling and/or thickening agent.

3. The oil-in-water emulsion as defined by claim 1, having a pH ranging from 5 to 7.

4. The oil-in-water emulsion as defined by claim 3, having a pH ranging from 5.5 to 6.5.

5. The oil-in-water emulsion as defined by claim 1, wherein said at least one polymeric emulsifier is a crosslinked anionic amphiphilic polymer.

6. The oil-in-water emulsion as defined by claim 1, said anionic amphiphilic polymer comprising the copolymerizate of olefinically unsaturated carboxylic and $C_{10}$–$C_{30}$ alkyl ester comonomers.

7. The oil-in-water emulsion as defined by claim 5, said anionic amphiphilic polymer being crosslinked with olefinically unsaturated and non-conjugated polyolefinically unsaturated comonomers.

8. The oil-in-water emulsion as defined by claim 7, said non-conjugated polyolefinically unsaturated comonomer comprising a polyallyl ether.

9. The oil-in-water emulsion as defined by claim 5, said crosslinked anionic amphiphilic polymer comprising from 95% to 60% by weight of recurring acrylic structural units, from 4% to 40% by weight of recurring acrylate structural units, and 0.1% to 6% by weight of a crosslinking comonomer, wherein said percentages are relative to the total weight of said emulsion.

10. The oil-in-water emulsion as defined by claim 5, said crosslinked anionic amphiphilic polymer comprising from 98% to 96% by weight of recurring acrylic structural units, from 1% to 4% by weight of recurring acrylate structural units, and 0.1% to 0.6% by weight of a crosslinking comonomer, wherein said weight percentages are relative to the total weight of said emulsion.

11. The oil-in-water emulsion as defined by claim 1, comprising up to 1% by weight of said at least one emulsifying agent (b).

12. The oil-in-water emulsion as defined by claim 11, comprising from 0.2% to 0.4% by weight of said at least one emulsifying agent (b).

13. The oil-in-water emulsion as defined by claim 1, said at least one glycol (a) comprising a glycol, which promotes penetration of said emulsion into the skin selected from a glycol selected from the group consisting of propylene glycol, dipropylene glycol, propylene glycol dipelargonate, lauroglycol and ethoxydiglycol.

14. The oil-in-water emulsion as defined by claim 13, comprising from 40% to 50% by weight relative to the total weight of said emulsion of said at least one glycol (a).

15. The oil-in-water emulsion as defined by claim 2, said at least one biologically active agent is selected from the group consisting of (c) an agent which modulates at least one of skin differentiation, proliferation and pigmentation; an antibacterial agent, an antiparasitic agent, an antifungal agent, a steroidal anti-inflammatory agent, a non-steroidal anti-inflammatory agent, an anaesthetic agent, an antipruritic agent, an antiviral agent, a keratolytic agent, an anti-free radical agent, an antiseborrhoeic agent, an antidandruff agent, an anti-acne agent, an antimetabolite, an agent for combating hair loss, an antiseptic and combinations thereof.

16. The oil-in-water emulsion as defined by claim 15, comprising from 0.0001% to 20% by weight relative to the total weight of said emulsion of said at least one biologically active agent (c).

17. The oil-in-water emulsion as defined by claim 1, comprising from 5% to 50% by weight relative to the total weight of said emulsion of an oily phase.

18. The oil-in-water emulsion as defined by claim 17, comprising from 10% to 70% by weight of an aqueous phase relative to the total weight of said emulsion.

19. The composition of claim 1, wherein said anionic amphiphilic polymer comprises recurring acrylic structural units and acrylate structural units.

20. The composition of claim 2, wherein said anionic amphiphilic polymer is cross-linked.

* * * * *